(12) United States Patent
Meissner et al.

(10) Patent No.: US 6,403,310 B1
(45) Date of Patent: *Jun. 11, 2002

(54) HUMAN INOSITOL MONOPHOSPHATASE H1

(75) Inventors: Paul S. Meissner, Barnesville; Jeannine D. Gocayne, Potomac, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,198

(22) Filed: May 19, 1999

Related U.S. Application Data

(60) Division of application No. 09/002,072, filed on Feb. 9, 1998, which is a division of application No. 08/461,731, filed on Jun. 5, 1995, now Pat. No. 5,955,339, which is a continuation-in-part of application No. PCT/US94/10465, filed on Sep. 16, 1994, now Pat. No. 5,716,806.

(51) Int. Cl.$^7$ .............................. C12Q 1/68; C12N 9/16; C12N 1/20; C12N 15/00; C07K 1/00

(52) U.S. Cl. ..................... 435/6; 435/196; 435/240.2; 435/252.3; 435/320.1; 536/23.2; 536/23.5; 530/350

(58) Field of Search ..................... 435/6, 196, 240.2, 435/252.3, 320.1; 536/23.2, 23.5; 530/350

(56) References Cited

U.S. PATENT DOCUMENTS 4,981,980 A    1/1991    Giocobbe et al. ........... 549/345

FOREIGN PATENT DOCUMENTS

WO    WO 93/25692    12/1993

OTHER PUBLICATIONS

Kofman et al., Biological Psychiatry, 34:839–852 (1993).

McAllister, G. et al., Biochemical Journal, 284:749–754 (1992).

Atack, J. et al., Brain Research, 613:305–308 (1993).

Majerus, P. et al., Cell, 63:459–465 (1990).

Majerus, P., Annual Review of Biochemistry, 61:225–250 (1992).

York, J. et al., PNAS, USA, 90:5833–5837 (1993).

Wreggett, K., Biochemical Journal, 286:147–152 (1992).

*Primary Examiner*—Ponnathapu Achutamurthy
*Assistant Examiner*—Tekchand Saidha
(74) *Attorney, Agent, or Firm*—Human Genome Sciences, Inc.

(57) ABSTRACT

Human inositol monophosphatase H1 polynucleotide and DNA (RNA) encoding such polypeptides and a procedure for producing such polypeptides by recombinant techniques and utilizing such polypeptide for therapeutic purposes, for example, screening and designing compounds capable of inhibiting hIMP-H1 and mapping genetic diseases are disclosed. Also disclosed are antagonists against such polypeptide along with procedures for using such antagonists for therapeutic purposes, for example, for treating psychotic and depressive disorders. Diagnostic assays for identifying mutations in nucleic acid sequence encoding a polypeptide of the present invention and for detecting altered levels of the polypeptide of the present invention are also disclosed.

61 Claims, 8 Drawing Sheets

```
            atgtgcaccacagggggcggggctggagatcatcagaaaagcccttactgaggaaaaacgt
     83   ----------+---------+---------+---------+---------+---------+ 142
            tacacgtggtgtccccgccccgacctctagtagtcttttcgggaatgactccttttttgca
     b       M  C  T  T  G  A  G  L  E  I  I  R  K  A  L  T  E  E  K  R gtctcaacaaaaacatcagctgcagatcttgtgacagaaacagatcaccttgtggaagat
    143   ----------+---------+---------+---------+---------+---------+ 202
            cagagttgttttttgtagtcgacgtctagaacactgtctttgtctagtggaacaccttcta
     b       V  S  T  K  T  S  A  A  D  L  V  T  E  T  D  H  L  V  E  D ttaattatttctgagttgcgagagaggtttccttcacacaggttcattgcagaagaggcc
    203   ----------+---------+---------+---------+---------+---------+ 262
            aattaataaagactcaacgctctctccaaaggaagtgtgtccaagtaacgtcttctccgg
     b       L  I  I  S  E  L  R  E  R  F  P  S  H  R  F  I  A  E  E  A gcggcttctggggccaagtgtgtgctcacccacagcccgacgtggatcatcgaccccatc
    263   ----------+---------+---------+---------+---------+---------+ 322
            cgccgaagaccccggttcacacacgagtgggtgtcgggctgcacctagtagctggggtag
     b       A  A  S  G  A  K  C  V  L  T  H  S  P  T  W  I  I  D  P  I
                                                                  _____ gacggcacctgcaattttgtgcacagattcccgactgtggcggttagcattggatttgct
    323   ----------+---------+---------+---------+---------+---------+ 382
            ctgccgtggacgttaaaacacgtgtctaagggctgacaccgccaatcgtaacctaaacga
     b       D  G  T  C  N  F  V  H  R  F  P  T  V  A  V  S  I  G  F  A
             _____
```

FIG. 1A

```
             gttcgacaagagcttgaattcggagtgatttaccactgcacagaggagcggctgtacacg
      383 ----------+---------+---------+---------+---------+---------+ 442
             caagctgttctcgaacttaagcctcactaaatggtgacgtgtctcctcgccgacatgtgc
    b         V  R  Q  E  L  E  F  G  V  I  Y  H  C  T  E  E  R  L  Y  T ggccggcggggtcggggcgccttctgcaatggccagcggctccgggtctccggggagaca
      443 ----------+---------+---------+---------+---------+---------+ 502
             ccggccgccccagccccgcggaagacgttaccggtcgcggaggcccagaggcccctctgt
    b          G  R  R  G  R  G  A  F  C  N  G  Q  R  L  R  V  S  G  E  T gatctctcaaaggccttggttctgacagaaattggccccaaacgtgaccctgcgaccctg
      503 ----------+---------+---------+---------+---------+---------+ 562
             ctagagagtttccggaaccaagactgtctttaaccggggtttgcactgggacgctgggac
    b          D  L  S  K  A  L  V  L  T  E  I  G  P  K  R  D  P  A  T  L aagctgttcctgagtaacatggagcggctgctgcatgccaaggcgcatggggtccgagtg
      563 ----------+---------+---------+---------+---------+---------+ 622
             ttcgacaaggactcattgtacctcgccgacgacgtacggttccgcgtaccccaggctcac
    b          K  L  F  L  S  N  M  E  R  L  L  H  A  K  A  H  G  V  R  V attggaagctccacattggcactctgccacctggcctcaggggccgcggatgcctattac
      623----------+---------+---------+---------+---------+---------+ 682
             taaccttcgaggtgtaaccgtgagacggtggaccggagtccccggcgcctacggataatg
    b          I  G  S  S  T  L  A  L  C  H  L  A  S  G  A  A  D  A  Y  Y
```

FIG. 1B

```
       cagtttggcctgcactgctgggatctggcggctgccacagtcatcatcagagaagcaggc
   683 ---------+---------+---------+---------+---------+---------+ 742
       gtcaaaccggacgtgacgaccctagaccgccgacggtgtcagtagtagtctcttcgtccg
 b      Q  F  G  L  H  C  W  D  L  A  A  A  T  V  I  I  R  E  A  G ggcatcgtgatagacacttcggggtggaccccctcgacctcatggtttgcagagtggttgcg
   743 ---------+---------+---------+---------+---------+---------+ 802
       ccgtagcactatctgtgaagcccacctggggagctggagtaccaaacgtctcaccaacgc
 b      G  I  V  I  D  T  S  G  G  P  L  D  L  M  V  C  R  V  V  A gccagcacccgggagatggcgatgctcatagctcaggccttacagacgattaactatggg
   803 ---------+---------+---------+---------+---------+---------+ 862
       cggtcgtgggccctctaccgctacgagtatcgagtccggaatgtctgctaattgataccc
 b      A  S  T  R  E  M  A  M  L  I  A  Q  A  L  Q  T  I  N  Y  G cgggatgatgagaagtga
   863 ---------+-------- 880
       gccctactactcttcact
 b      R  D  D  E  K  *
```

1   GGATCCAGGA GTTGGAGCCC GCCTGCGCGC TGCGGGACGG GGCACGGGCGG
51  AAGGGTTGGG TCCGCCTCGA GCGGGGAGGG TAATGTGCAC CACAGGGGCG
101 GGGCTGGAGA TCATCAGAAA AGCCCTTACT GAGGAAAAAC GTGTCTCAAC
151 AAAAACATCA GCTGCAGATC TTGTGACAGA AACAGATCAC CTTGTGGAAG
201 ATTTAATTAT TTCTGAGTTG CGAGAGAGGT TTCCTTCACA CAGGTTCATT
251 GCAGAAGAGG CCGGCGGCTTC TGGGGCCAAG TGTGTGCTCA CCCACAGCCC
301 GACGTGGATC ATCGACCCCA TCGACGGCAC CTGCAATTTT GTGCACAGAT
351 TCCCGACTGT GGCGGTTAGC ATTGGATTTG CTGTTCGACA AGAGCTTGAA
401 TTCGGAGTGA TTTACCACTG CACAGAGGAG CGGCTGTACA CGGGCCGGCG
451 GGGTCGGGGC GCCTTCTGCA ATGGCCAGCG GCTCCGGGTC TCCGGGGAGA

FIG. 2B

```
501  CAGATCTCTC AAAGGCCTTG GTTCTGACAG AAATTGGCCC CAAACGTGAC
551  CCTGCGACCC TGAAGCTGTT CCTGAGTAAC ATGGAGCGGC TGCTGCATGC
601  CAAGGGGCAT GGGGTCCGAG TGATTGGAAG CTCCACATTG GCACTCTGCC
651  ACCTGGCCTC AGGGGCCGCG GATGCCTATT ACCAGTTTGG CCTGCACTGC
701  TGGGATCTGG CGGCTGCCAC AGTCATCATC AGAGAAGCAG GCGGCATCGT
751  GATAGACACT TCGGGTGGAC CCCTCGACCT CATGGTTTGC AGAGTGGTTG
801  CGGCCAGCAC CCGGGAGATG GCGATGCTCA TAGCTCAGGC CTTACAGACG
851  ATTAACTATG GGCGGGATGA TGAGAAGTGA CTGCGGGCTGA GGCAAAGCTG
901  CTCCCAAGGC CTCCCTGGGC TGCTGTGGGC TCCTGGGGAG GTGCCCCTCG
951  TGGCCCACGC TCCATGCCAG TGGCTCACGC TCTGCTCCTG GCTACGCCAG
```

```
1001  AGGGAGTTGT  CACGCTACAG  TGAGTGGCTG  GCCTTTTAAA  TCGACGTCTC
1051  TCTCACCAGG  ATTTGGTGTT  TAGCTGTTTC  TCTCTTTAAT  CTCACGTAGC
1101  CCTTTTTCAG  GTTAGTACGT  GTTCTTCTGT  CAGGGCAAAA  CTCAAATCTC
1151  CTGTGAAATA  CGTATTGATA  ATCCAATCTT  GATTTTCCC   CCCAGAATAT
1201  AAATCTCAGG  TAATAAGGCT  TTAGAACTGC  TGATAAAGGG  ATCGTTCTCA
1251  GGCCTCCCCC  CGGAGTACTT  CAGAATGCAA  TAAATCAAAA  TATGGGAAAA
1300  AAAAAACTCG  AG
```

```
                                                                    50
hIMPff    MADPWQECMD YAVTLARQAG EVVCEAIKNE MNVMIKSSPV DLVTPTDQKV
hIMP-H1                         MCTTGAGL EIIRKALTEE KFVSTKIISAA DLVTFTDHLV  38
Consensus ..........  ..........  .E..... A...... .V....K.S. DLVTI.TD..V   50

100
hIMPff    EKMIISSIKE KYPSHEFICE ESVAAGEKSI LIDNPTWIID PIDGTINFVH         100
hIMP-H1   EDLISELRE RFPSHEFIFE EAAASCNKCV LTHSPTWIID PIDGTONFVH           88
Consensus E....IS...E .PSH.FI.E E.....A.G.K.. LI..PTWIID PIDGT.NFVH       100

150
hIMPff    RFPFVAVSIG FAVNKKIEFG VMYSCVEGKM YTPRKGGAF CNGQKLVSQ           150
hIMP-H1   RFPIVAVSIG FAVRQELEFG VIYRCHEERL YTGRFGGAF CNGQHLVSG           138
Consensus RFP.VAVSIG FAV....EFG V.Y.C.E... YT.R.G.GAF CNGQ.L.VS.          150
``` hIMPff
hIMP-H1
Consensus hIMPff
hIMP-H1
Consensus hIMPff
hIMP-H1
Consensus

FIG. 3B

```
hIMPff     QEDITKSILV TEIGSSRIIPE TVRMVLSNME KIFCIPVHGI RSVGTAAVNM    200
hIMP-H1    ETDLSKAIVL TEDGPKRIPA ILKLFLSNME FILHAKAHGV RVIGSSTLAL....  188
Consensus  ..D...K.I. TE.G...I.. I....LSNME .L........ .HG...R..G....   200 hIMPff     GLVAIGAADA YYENGIHCWD VAIAGIIVIE AGGVLMDVTG GPFDLMSHRV       250
hIMP-H1    CHLASGAADA YYQFGIHCWD IAIATVIIRE AGGIVIDTSG GPIDLMVCRV       238
Consensus  G..A.G.ADA YY....HCWD .A.A..II.E .AGG...D..G GP.DLM..RV       250 hIMPff     IAANNRIIAE RIAKEIQMIP LQRDDED--                             277
hIMP-H1    VAAASTREMAM LIAQALQIIN YGRDDEKX-                             266
Consensus  .AA..R..A. .IA...Q.I. ..RDDE...                             279
``` hIMPff
hIMP-H1
Consensus hIMPff
hIMP-H1
Consensus hIMPff
hIMP-H1
Consensus

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 798 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGTGCACCA CAGGGGCGGG GCTGGAGATC ATCAGAAAAG CCCTTACTGA GGAAAAACGT        60

GTCTCAACAA AAACATCAGC TGCAGATCTT GTGACAGAAA CAGATCACCT TGTGGAAGAT       120

TTAATTATTT CTGAGTTGCG AGAGAGGTTT CCTTCACACA GGTTCATTGC AGAAGAGGCC       180

GCGGCTTCTG GGGCCAAGTG TGTGCTCACC CACAGCCCGA CGTGGATCAT CGACCCCATC       240

GACGGCACCT GCAATTTTGT GCACAGATTC CCGACTGTGG CGGTTAGCAT TGGATTTGCT       300

GTTCGACAAG AGCTTGAATT CGGAGTGATT TACCACTGCA CAGAGGAGCG GCTGTACACG       360

GGCCGGCGGG GTCGGGGCGC CTTCTGCAAT GGCCAGCGGC TCCGGGTCTC CGGGGAGACA       420

GATCTCTCAA AGGCCTTGGT TCTGACAGAA ATTGGCCCCA AACGTGACCC TGCGACCCTG       480

AAGCTGTTCC TGAGTAACAT GGAGCGGCTG CTGCATGCCA AGGCGCATGG GGTCCGAGTG       540

ATTGGAAGCT CCACATTGGC ACTCTGCCAC CTGGCCTCAG GGGCCGCGGA TGCCTATTAC       600

CAGTTTGGCC TGCACTGCTG GGATCTGGCG GCTGCCACAG TCATCATCAG AGAAGCAGGC       660

GGCATCGTGA TAGACACTTC GGGTGGACCC CTCGACCTCA TGGTTTGCAG AGTGGTTGCG       720

GCCAGCACCC GGGAGATGGC GATGCTCATA GCTCAGGCCT TACAGACGAT TAACTATGGG       780

CGGGATGATG AGAAGTGA                                                     798
```

(2) INFORMATION FOR SEQ ID NO:2:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Cys Thr Thr Gly Ala Gly Leu Glu Ile Ile Arg Lys Ala Leu Thr
 1               5                  10                  15

Glu Glu Lys Arg Val Ser Thr Lys Thr Ser Ala Ala Asp Leu Val Thr
            20                  25                  30

Glu Thr Asp His Leu Val Glu Asp Leu Ile Ile Ser Glu Leu Arg Glu
        35                  40                  45

Arg Phe Pro Ser His Arg Phe Ile Ala Glu Ala Ala Ser Gly
    50                  55                  60

Ala Lys Cys Val Leu Thr His Ser Pro Thr Trp Ile Ile Asp Pro Ile
65                  70                  75                  80

Asp Gly Thr Cys Asn Phe Val His Arg Phe Pro Thr Val Ala Val Ser
                85                  90                  95

Ile Gly Phe Ala Val Arg Gln Glu Leu Glu Phe Gly Val Ile Tyr His
                100                 105                 110

Cys Thr Glu Glu Arg Leu Tyr Thr Gly Arg Arg Gly Arg Gly Ala Phe
                115                 120                 125

Cys Asn Gly Gln Arg Leu Arg Val Ser Gly Glu Thr Asp Leu Ser Lys
                130                 135                 140

Ala Leu Val Leu Thr Glu Ile Gly Pro Lys Arg Asp Pro Ala Thr Leu
145                 150                 155                 160

Lys Leu Phe Leu Ser Asn Met Gly Arg Leu Leu His Ala Lys Ala His
                165                 170                 175

Gly Val Arg Val Ile Gly Ser Ser Thr Leu Ala Leu Cys His Leu Ala
                180                 185                 190

Ser Gly Ala Ala Asp Ala Tyr Tyr Gln Phe Gly Leu His Cys Trp Asp
                195                 200                 205

Leu Ala Ala Ala Thr Val Ile Ile Arg Glu Ala Gly Gly Ile Val Ile
                210                 215                 220

Asp Thr Ser Gly Gly Pro Leu Asp Leu Met Val Cys Arg Val Val Ala
225                 230                 235                 240

Ala Ser Thr Arg Glu Met Ala Met Leu Ile Ala Gln Ala Leu Gln Thr
                245                 250                 255

Ile Asn Tyr Gly Arg Asp Asp Glu Lys
                260                 265
```

(2) INFORMATION FOR SEQ ID NO:3:

(i) SEQUENCE CHARACTERISTICS:
        (A) LENGTH: 1313 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GGATCCAGGA GTTGGAGCCC GCCTGCGCGC TGCGGGACGG GGCACGGCGG AAGGGTTGGG    60
```

```
TCCGCCTCGA GCGGGGAGGG TAATGTGCAC CACAGGGGCG GGGCTGGAGA TCATCAGAAA      120

AGCCCTTACT GAGGAAAAAC GTGTCTCAAC AAAAACATCA GCTGCAGATC TTGTGACAGA      180

AACAGATCAC CTTGTGGAAG ATTTAATTAT TTCTGAGTTG CGAGAGAGGT TTCCTTCACA      240

CAGGTTCATT GCAGAAGAGG CCGCGGCTTC TGGGGCCAAG TGTGTGCTCA CCCACAGCCC      300

GACGTGGATC ATCGACCCCA TCGACGGCAC CTGCAATTTT GTGCACAGAT TCCCGACTGT      360

GGCGGTTAGC ATTGGATTTG CTGTTCGACA AGAGCTTGAA TTCGGAGTGA TTTACCACTG      420

CACAGAGGAG CGGCTGTACA CGGGCCGGCG GGGTCGGGGC GCCTTCTGCA ATGGCCAGCG      480

GCTCCGGGTC TCCGGGGAGA CAGATCTCTC AAAGGCCTTG GTTCTGACAG AAATTGGCCC      540

CAAACGTGAC CCTGCGACCC TGAAGCTGTT CCTGAGTAAC ATGGAGCGGC TGCTGCATGC      600

CAAGGCGCAT GGGGTCCGAG TGATTGGAAG CTCCACATTG GCACTCTGCC ACCTGGCCTC      660

AGGGGCCGCG GATGCCTATT ACCAGTTTGG CCTGCACTGC TGGGATCTGG CGGCTGCCAC      720

AGTCATCATC AGAGAAGCAG GCGGCATCGT GATAGACACT TCGGGTGGAC CCCTCGACCT      780

CATGGTTTGC AGAGTGGTTG CGGCCAGCAC CCGGGAGATG GCGATGCTCA TAGCTCAGGC      840

CTTACAGACG ATTAACTATG GCGGGATGAT GAGAAGTGA CTGCGGCTGA GGCAAAGCTG      900

CTCCCAAGGC CTCCCTGGGC TGCTGTGGGC TCCTGGGGAG GTGGCCCTCG TGGCCCACGC      960

TCCATGCCAG TGGCTCACGC TCTGCTCCTG GCTACCCCAG AGGGAGTTGT CACGCTACAG     1020

TGAGTGGCTG GCCTTTTAAA TCGACGTCTC TCTCACCAGG ATTTGGTGTT TAGCTGTTTC     1080

TCTCTTTAAT CTCACGTAGC CCTTTTTCAG GTTAGTACGT GTTCTTCTGT CAGGGCAAAA     1140

CTCAAATCTC CTGTGAAATA CGTATTGATA ATCCAATCTT GATTTTTCCC CCAGAATAT      1200

AAATCTCAGG TAATASAGGC TTTAGAACTG CTGATAAAGG GATCGTTCTC AGGCCTCCCC     1260

CCGGAGTACT TCAGAATGCA ATAAATCAAA ATATGGGAAA AAAAAAACTC GAG            1313

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ACTTGCTACG GATCCATGTG CACCACAGGG GCG                                    33

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ACTTGCTACA AGCTTTCACT TCTCATCATC CCG                                    33

(2) INFORMATION FOR SEQ ID NO:6:

(i) SEQUENCE CHARACTERISTICS:
        (A) LENGTH: 35 base pairs
        (B) TYPE: nucleic acid
```

(C) STRANDEDNESS: single
            (D) TOPOLOGY: linear (ii) MOLECULE TYPE: DNA (genomic)

(xi) SEQUENCE DESCRIPTION: SEQ ID NO:6:

CCGGATCCGC CACCATGTGC ACCACAGGGG CGGGG                      35

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

CACAGGTACC CAGCTTTGCC TCAGCCGCAG                             30

(2) INFORMATION FOR SEQ ID NO:8:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CCGGATCCGC CACCATGTGC ACCACAGGGG CGGGG                      35

(2) INFORMATION FOR SEQ ID NO:9:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

CGCTCTAGAT CAAGCGTAGT CTGGGACGTC GTATGGGTAC TTCTCATCAT CCCGCCC    57

(2) INFORMATION FOR SEQ ID NO:10:

(i) SEQUENCE CHARACTERISTICS:
            (A) LENGTH: 127 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:10:

Gln Glu Asp Ile Thr Lys Ser Leu Leu Val Thr Glu Leu Gly Ser Ser
1               5                   10                  15

Arg Thr Pro Glu Thr Val Arg Met Val Leu Ser Asn Met Glu Lys Leu
                20                  25                  30

Phe Cys Ile Pro Val His Gly Ile Arg Ser Val Gly Thr Ala Ala Val
                35                  40                  45

Asn Met Cys Leu Val Ala Thr Gly Gly Ala Asp Ala Tyr Tyr Glu Met
50                  55                  60

-continued

```
Gly Ile His Cys Trp Asp Val Ala Gly Ala Gly Ile Ile Val Thr Glu
65                  70                  75                  80

Ala Gly Gly Val Leu Met Asp Val Thr Gly Gly Pro Phe Asp Leu Met
                85                  90                  95

Ser Arg Arg Val Ile Ala Ala Asn Asn Arg Ile Leu Ala Glu Arg Ile
                100                 105                 110

Ala Lys Glu Ile Gln Val Ile Pro Leu Gln Arg Asp Asp Glu Asp
        115                 120                 125
```

HUMAN INOSITOL MONOPHOSPHATASE H1

This application is a Divisional of U.S. application Ser. No. 09/002,072, filed Feb. 9, 1998 now U.S. Pat. 5,955,339, which is a divisional of U.S. application Ser. No. 08/461,731, filed Jun. 6, 1995, now U.S. Pat. No. 5,716,806, which is a continuation-in-part of U.S. application Ser. No. PCT/US94/10465 filed on Sep. 16, 1994, now abandoned.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human Inositol Monophosphatase H1, sometimes hereinafter referred to as "hIMP-H1". The invention also relates to inhibiting the action of such polypeptides.

Cells respond to extracellular stimuli through complicated networks of responses. Inositol lipid metabolism plays a key role in intracellular signalling. Agonist-induced stimulation of cells releases the signalling molecules diacylglycerol and inositol polyphosphates via phospholipase C hydrolysis of phosphoinositides. Diacylglycerol functions to stimulate protein kinase C (Nishizuka, Y., *Science*, 233:305–312 (1986), and several inositol polyphosphates, most notably inositol 1, 4, 5-triphosphate evoke the release of intracellular and intercellular calcium (Berridge, M. J. and Irvine, R. F., *Nature*, (London), 312, 315–321 (1984). Action of inositol phosphatases and kinases gives rise to a plethora of inositol phosphates (Majerus, P. W. et al., *J. Biol. Chem.*, 263:3051–3054 (1988) in the cytosol that may also serve as signalling or regulatory molecules.

Inositol monophosphatase (IMP) plays an important role in the phosphatidylinositol signalling pathway by catalyzing the hydrolysis of inositol monophosphates. IMP's are believed to be the molecular site of action for lithium therapy for manic-depressive illness. Lithium inhibits inositol monophosphatase and prevents the accumulation of free inositol from inositol-1-phosphate.

Lithium carbonate was shown to be an effective antimanic compound by John Cade in 1949, and this compound was approved for wide-spread use in 1969. However, treatment of manic-depressive patients with lithium is associated with certain deleterious side effects. These include tremor, weight gain, diarrhea, skin rash, transient leukocytosis, hypothyroidism, and polyuria-polydipsia. Additional clinical ailments associated with chronic lithium therapy are structural lesions in the kidney (including tubular atrophy, glomerular sclerosis and interstitial fibrosis). These side effects are directly due to lithium toxicity.

The phosphoinositide (PI) cycle is a likely target for lithium action, since it has been demonstrated that a profound elevation of inositol-1-phosphate and a corresponding decrease in free inositol in the brains of rats occurred when treated systemically with lithium. This was attributed to inhibition of inositol-1-phosphate phosphatase and led to the hypothesis that lithium was able to damp down the activity of the PI cycle in overstimulated cells, thus explaining its effectiveness in controlling mania.

Provision of inositol for the PI cycle can come from hydrolysis of inositol phosphates, by de novo synthesis from glucose, or from the diet. The former processes are dependent on the operation of inositol-1-phosphate phosphatase and are, therefore, inhibited by lithium. Dietary inositol can bypass lithium blockade in peripheral tissues but not in the CNS, since inositol does not cross the blood brain barrier. Thus, the increase in inositol-1-phosphate in brain is accompanied by an equivalent decrease in free inositol.

Manganese supports catalysis by inositol monophosphatase. on the other hand, divalent ions, i.e., calcium and manganese, are competitive inhibitors (Hallcher, L. M. and Sherman, W. R., *J. Biol. Chem.*, 255:10896–901 (1980)). Lithium inhibits inositol monophosphate phosphatase uncompetitively.

IMP liberates inositol from the substrates INS (1) P, INS (3) P and INS (4) P. IMP is also capable of hydrolyzing various non-inositol containing substrates including but not limited to those disclosed by Sherman, *J. Biol. Chem.*, 224:10896–10901 (1980), Takimoto, *J. Bio. Chem.* (Tokyo), 98:363–370 (1985) and by Gee, *Bio. Chem J.*, 249:883–889 (1988). The first human IMP cDNA was isolated and is disclosed by McAllister et al., (WO 93/25692 (1993)).

The polypeptide of the present invention has been putatively identified as a human inositol monophosphatase polypeptide. This identification has been made as a result of amino acid sequence homology.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptides, or polynucleotides encoding such polypeptides for therapeutic purposes, for example, for screening and designing compounds capable of inhibiting this class of enzymes, and for the treatment of psychiatric disorders.

In accordance with yet a further aspect of the present invention, there is provided an antibody against such polypeptides.

In accordance with yet another aspect of the present invention, there are provided antagonists against such polypeptides, which may be used to inhibit the action of such polypeptides, for example, in the treatment of psychotic and depressive disorders (bipolar and non-bipolar).

In accordance with yet a further aspect of the present invention, there is also provided nucleic acid probes comprising nucleic acid molecules of sufficient length to specifically hybridize to a nucleic acid sequence of the present invention.

In accordance with still another aspect of the present inventions there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

BRIEF DESCRIPTION OF THE DRAWING

The following drawings are illustrative of embodiments of the invention and are not meant to limit the scope of the invention as encompassed by the claims.

FIGS. 1A, 1B and 1C collectively show the polynucleotide sequence (SEQ ID NO:1) and its complement as well as the corresponding deduced amino acid sequence (SEQ ID NO:2) for the putative mature human inositol monophosphate H1 polypeptide, wherein FIG. 1A illustrates the first portions of the polynucleotide sequence of the cDNA encoding the of the putative mature human inositol monophosphate H1 polypeptide, its complement and its deduced amino acid sequence and FIGS. 1B–1C consecutively continue with their respective parts to the end of the same polynucleotide, its complement and amino acid sequences. The standard one-letter abbreviations for amino acid residues are used to illustrate the amino acid sequence in FIGS. 1A–C.

FIGS. 2A, 2B and 2C collectively show the polynucieotide sequence (SEQ ID NO:1) for the putative human inositol monophosphate H1 polypeptide, wherein FIG. 2A illustrates the first portion of the polynucleotide sequence of the cDNA encoding the mature putative human inositol monophosphate H1 polypeptide and FIGS. 2B–2C consecutively continue with their respective parts to the end of the same polynucleotide sequence.

FIGS. 3A and 3B collectively show the amino acid homology between the hIMP polypeptide (top line of each comparative row; SEQ ID NO:10); the hIMP-H1 polypeptide of the present invention (second line of each comparative row; SEQ ID NO:2); and the consensus sequence (common amino acids boxed and bottom line of each comparative row). Wherein FIG. 3A illustrates the first portions of the hIMP polypeptide in the top line of each comparative row and the first portions of the hIMP-H1 polypeptide in the second line of each comparative row and FIG. 3B consecutively continues with the ends of the same two amino acid sequences. The standard one-letter abbreviations for amino acid residues are used to illustrate the amino acid sequences in FIGS. 3A–B.

Sequencing inaccuracies are a common problem when attempting to determine polynucleotide sequences. Accordingly, the sequence of FIGS. 1A–1C collectively is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIGS. 1A–1C collectively (SEQ ID NO:2) or for the mature polypeptide encoded by the cDNA of the clone deposited as ATCC Deposit No. 75753 on Apr. 25, 1994. And, this ATCC number is directed to a biological deposit with the American Tissue Culture Collection, 10801 University Blvd., Manassas, Va. 20110-2209, USA. The strain referred to is being maintained under the terms of the Budapest Treaty and will be made available to a patent office signatory to the Budapest Treaty.

A polynucleotide encoding a polypeptide of the present invention may be obtained from human brain, lymphocytes and placenta. The polynucleotide of this invention was discovered in a cDNA library derived from human brain tissue. It is structurally related to the inositol phosphatase family. It contains an open reading frame encoding a protein of about 265 amino acid residues. The protein exhibits the highest degree of homology to human inositol monophosphatase with 55% identity and 65% similarity over a 265 amino acid stretch. It is also important that the amino acid sequence DPIDGT is conserved in the polypeptide of the present invention, since this region has been shown to be essential at the active site of IMP enzymes.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1C (SEQ ID NO:1) or that of the deposited clone or may be a different coding sequence which coding sequence, as a result of the redundancy or degeneracy of the genetic code, encodes the same mature polypeptide as the DNA of FIGS. 1A–1C (SEQ ID NO:1) or the deposited cDNA.

The polynucleotide which encodes for the mature polypeptide of FIGS. 1A–1C (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1C (SEQ ID NO:2) or the same mature polypeptide encoded by the cDNA of the deposited clone as well as variants of such polynucleotides which variants encode for a fragment, derivative or analog of the polypeptide of FIGS. 1A–1C (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1C (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1C (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 1A–1C or which has the amino acid sequence encoded by the deposited cDNA, as well as fragments, analogs and derivatives of such polypeptide.

The terms "fragment," "derivative" and "analog" when referring to the polypeptide of FIGS. 1A–1C (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1C (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hIMP-H1 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, $Salmonella$ $typhimurium$; fungal cells, such as yeast; insect cells such as Drosophila and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CKV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3(Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian. expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The hIMP-H1 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

hIMP-H1 may be employed to design alternative therapeutic compounds, other than lithium, for manic-depressive illnesses. hIMP-H1 is therefore useful for screening and designing compounds capable of inhibiting hIMP-H1.

hIMP-H1 may also be employed to map genetic diseases. For example, the exact genetic lesion(s) responsible for some forms of hereditary manic-depressive illness are still unknown but are the subject of intense investigation (York, et al., *PNAS USA*, 90:5833–5837, (1993)). One of the targets of this investigation is the IMP gene. The hIMP-H1 c.DNA can be employed to isolate the chromosomal locus of the complete gene. This region of the chromosome can then be tested to determine if any mutations in families affected by manic depression and possibly other psychiatric disorders are localized in this region.

The present invention relates to an assay which identifies compounds which block (antagonists) hIMP-H1 from functioning. In order to provide a structural basis from which to design alternative therapeutic compounds which inhibit hIMP-H1, the purification, cloning and X-ray crystallization of hIMP-H1 is undertaken. From the cloned enzyme structural data is generated, especially X-ray crystallographic and structural data is obtained and used to screen for and design antagonists to hIMP-H1. An example of such a screen includes measuring the release of [$^{14}$C]inositol from DL-Ins (1)P containing L-[U-$^{14}$C]Ins(1)P as label, as described in (Gumber et al., Plant Physiol., 76:40–44 (1989)). One unit of enzyme activity represents 1 $\mu$mol of substrate hydrolysed/min, at 37° C. Protein concentrations may be determined by the method of Bradford (Bradford, M., Anal. Biochem., 72:248–252 (1976)).

The above described assay may also be used to block the other enzymes which are critical to the PI cycle, for example, phosphoinositol kinases which are enzymes involved in the phosphatidylinositol signaling pathway, namely they catalyze the hydrolysis of the 1 position phosphate from inositol 1,3,4-triphosphate and inositol 1,4-biphosphate.

Potential antagonists include an antibody against the hIMP-H1 polypeptide which binds thereto making the hIMP-H1 polypeptide inaccessible to substrate.

Potential antagonists also include proteins which are mimetics of hIMP-H1 (a closely related protein which does not retain hIMP-H1 function) which recognize and bind to the receptor subtypes which hIMP-H1 normally binds. However, there is no second messenger response. In this manner, the function of the hIMP-H1 enzyme is prevented and the beneficial therapeutic effects of inhibiting hIMP-H1 are achieved. Examples of these proteins include, but are not limited to, oligonucleotides and small-peptide molecules.

Antisense technology may also be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of hIMP-H1. The antisense RNA oligonucleotide hybridizes to the mRNA in vivo and blocks translation of the mRNA molecule into the hIMP-H1 (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hIMP-H1.

Another potential antagonist is a small molecule which binds to and occupies the catalytic site of the hIMP-H1 enzyme thereby making the catalytic site inaccessible to a substrate such that normal biological activity is prevented. Examples of small molecules include but are not limited to small peptides or peptide-like molecules.

The antagonists may be employed to treat psychotic and depressive disorders (bipolar and non-bipolar) other than mania. The antagonists may be employed in a composition with a pharmaceutically acceptable carrier, e.g., as hereinafter described.

The compounds which inhibit the action of hIMP-H1 may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, the amount administered is an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The compounds identified which inhibit hIMP-H1 and which are polypeptides may also be employed in accordance with the present invention by expression of such polypeptides in viva, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniaues*, Vol. 7, No. 9, 980–990 (1989), or any other promoter (e.g., cellular promoters such as eukaryotic cellular promoters including, but not limited to, the histone, pol III, and $\beta$-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of hIMP-HI Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., *Nature*, 324:163–166 (1986)) prior to analysis. RNA or cDNA may also be used for the same purpose. As an example, PCR primers complementary to the nucleic acid encoding hIMP-H1 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the hIMP-H1 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled hIMP-HI and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial EBression and Purification of hIMP-H1

The DNA sequence encoding for hIMP-H1, ATCC #75753, is initially amplified using PCR oligonucleotide primers corresponding to the 5' end sequences of the processed hIMP-H1 protein (minus the signal peptide sequence) and the vector sequences 3' to the hIMP-H1 gene. Additional nucleotides corresponding to hIMP-H1 were added to the 5' and 3' sequences respectively. The 5' oligonucleotide primer has the sequence 5' ACTTGCTACGGATCCATGTGCAC-CACAGGGGCG 3' (SEQ ID NO:4) contains a Bam HI restriction enzyme site followed by 18 nucleotides of hIMP-H1 coding sequence starting from the presumed terminal amino acid of the processed protein codon. The 3' sequence 5' AGCTACAAGCCACCTCATCATCCCG 3' (SEQ ID NO:5) contains a Hind III site and is followed by 18 nucleotides of hIMP-H1 including the final stop codon. The restriction enzymes sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Bam H1 and Hind III. The amplified sequences were ligated into pQE-9 and were inserted in frame with the sequence encoding for the histidine tag and the RBS. The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the laci repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized hIMP-H1 was purified from this solution by chromatography on a Nickel-Chelate column under conditions that allow for tight binding by proteins containing the 6-His tag (Hochuli, E. et al., J. Chromatography 411:177–184 (1984). hIMP-H1 (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mnolar glutathione (oxidized). After incubation in this solution for 12 hours the protein was dialyzed to 10 mmolar sodium phosphate.

EXAMPLE 2

Cloning and Expression of hIMP-H1 Using the Baculovirus Expression System

The DNA sequence encoding the full length hIMP-H1protein, ATCC #75753, was amplified using PCR oligonucleotide primers corresponding to the 5' and 3' sequences of the gene:

The 5' primer has the sequence 5° CCGGATCCGCCACC ATGTGCACCACAGGGGCGGGG 3' (SEQ ID NO:6) contains a Bam H1 restriction enzyme site (in bold) followed by 6 nucleotides resembling an efficient signal for the initiation of translation in eukaryotic cells (Kozak, M., J. Mol. Biol., 196:947–950 (1987) and is just behind the first 21 nucleotides of the hIMP-H1 gene (the initiation codon for translation "ATG" is underlined).

The 3' primer has the sequence 5° CACAGGTAC-CCAGCTT TGCCTCAGCCGCAG 3' (SEQ ID NO:7) contains the cleavage site for the restriction endonuclease Asp718 and 20 nucleotides complementary to the 3' non-translated sequence of the hIMP-H1 gene. The amplified sequences were isolated from a 1% agarose gel using a commercially available kit ("Geneclean," BIO 101 Inc., La Jolla, Calif.). The fragment was then digested with the endonucleases Bam H1 and Asp718 and then purified again on a 1% agarose gel. This fragment is designated F2.

The vector pRG1 (modification of pVL941 vector, discussed below) is used for the expression of the hIMP-H1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam H1 and Asp718. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes Bam H1 and Asp718 then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBachIMP-H1) with the hIMP-H1 gene using the enzymes Bam H1 and Asp718. The sequence of the cloned fragment was confirmed by DNA sequencing.

5 μg of the plasmid pBachIMP-H1 was cotransfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBachIMP-H1 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-hIMP-H1 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant hIMP-H1 in COS Cells

The expression of plasmid, hIMP-H1-HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire hIMP-H1 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding hIMP-H1, ATCC #75753, was constructed by PCR on the original EST cloned using two primers: the 5' primer 5' 5' CCGGATCCGCCACC ATGTGCACCACAGGGGCGGGG 3' (SEQ ID NO:8) and contains a Bam H1 restriction enzyme site (in bold), and 18 nucleotides of hIMP-H1 starting from the initiation codon (underlined); the 3, sequence CGCTCTAGATCAAGCG-TAGTCTGGGACGTCGTATGGGTACTT CTCATCATC-CCGCCC (SEQ ID NO:9) which contains complementary sequences to an XbaI restriction site, translation stop codon, HA tag and the last 18 nucleotides of the hIMP-H1 coding sequence (not including the stop codon). Therefore, the PCR product contains a hIMP-H1 coding sequence followed by HA tag fused in frame, a translation termination stop codon next to the HA tag, and a Bam H1 and XbaI site. The PCR amplified DNA fragment and the vector, pcDNAI/Amp, were digested with Bam H1 and Xba I restriction enzymes and ligated. The ligation mixture was transformed into E. coli strain SURE (available from,Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hIMP-H1, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the hIMP-H1 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 4

Exrression via Gene Therapy

Fibroblasts are obtained from a subject by skin biopsy. The resulting tissue is placed in tissue-culture medium and separated-into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claim is:

1. An isolated nucleic acid molecule comprising: a polynucleotide sequence encoding a fragment of the human inositiol monophosphatase polypeptide consisting of amino acid residues 1 to 265 of SEQ ID NO:2, wherein said fragment has inositiol monophosphatase activity.

2. The isolated nucleic acid molecule of claim 1, wherein said nucleic acid molecule is DNA.

3. The isolated nucleic acid molecule of claim 1, wherein said nucleic acid molecule is RNA.

4. The isolated nucleic acid molecule of claim 1, wherein said nucleic acid molecule is single-stranded.

5. An isolated nucleic acid molecule comprising a polynucleotide sequence complimentary to the polynucleotide sequence of claim 4.

6. The isolated nucleic acid molecule of claim 1, wherein said polynucleotide sequence comprises a heterologous polynucleotide sequence.

7. The isolated nucleic acid molecule of claim 6, wherein said heterologous polynucleotide sequence encodes a heterologous polypeptide.

8. A method for making a recombinant vector comprising inserting the isolated nucleic acid molecule of claim 1, into a vector.

9. A recombinant vector comprising the isolated nucleic acid molecule of claim 1.

10. The recombinant vector of claim 9, wherein said nucleic acid molecule is operably associated with a heterologous regulatory sequence that controls gene expression.

11. A recombinant host cell comprising the isolated nucleic acid molecule of claim 1.

12. The recombinant host cell of claim 11, wherein said nucleic acid molecule is operably associated with a heterologous regulatory sequence that controls gene expression.

13. A method for producing a polypeptide, comprising:
    (a) culturing a host cell under conditions suitable to produce a polypeptide encoded by the polynucleotide of claim 1; and
    (b) recovering the polypeptide from the cell culture.

14. An isolated nucleic acid molecule comprising: a polynucleotide sequence encoding at least 30 amino acid residues of the human inositiol monophospharase polypeptide consisting of residues 1 to 265 of SEQ ID NO:2.

15. The isolated nucleic acid molecule of claim 4, wherein said polynucleotide sequence encodes at least 50 amino acid residues of the human inositiol monophosphatase polypeptide consisting of amino acid residues 1 to 265 of SEQ ID NO:2.

16. The isolated nucleic acid molecule of claim 14, wherein said nucleic acid molecule is DNA.

17. The isolated nucleic acid molecule of claim 14, wherein said nucleic acid molecule is RNA.

18. The isolated nucleic acid molecule of claim 14, wherein said nucleic acid molecule is single-stranded.

19. An isolated nucleic acid molecule comprising a polynucleotide sequence complimentary to the polynucleotide sequence of claim 18.

20. The isolated nucleic acid molecule of claim 14, wherein said polynucleotide sequence comprises a heterologous polynucleotide sequence.

21. The isolated nucleic acid molecule of claim 20, wherein said heterologous polynucleotide sequence encodes a heterologous polypeptide.

22. A method for making a recombinant vector comprising inserting the isolated nucleic acid molecule of claim 21 into a vector.

23. A recombinant vector comprising the isolated nucleic acid molecule of claim 14.

24. The recombinant vector of claim 23, wherein said nucleic acid molecule is operably associated with a heterologous regulatory sequence that controls gene expression.

25. A recombinant host cell comprising the isolated nucleic acid molecule of claim 14.

26. The recombinant host cell of claim 25, wherein said nucleic acid molecule is operably associated with a heterologous regulatory sequence that controls gene expression.

27. A method for producing a polypeptide comprising:
    (a) culturing a host cell under conditions suitable to produce a polypeptide encoded by the polynucleotide of claim 14; and
    (b) recovering the polypeptide from the cell culture.

28. An isolated nucleic acid molecule comprising: a polynucleotide sequence encoding a fragment of a human inositiol monophosphatase polypeptide encoded by the human cDNA clone contained in ATCC Deposit No. 75753, wherein said polypeptide fragment has inositiol monophosphatase activity.

29. The isolated nucleic acid molecule of claim 28, wherein said nucleic acid molecule is DNA.

30. The isolated nucleic acid molecule of claim 28, wherein said nucleic acid molecule is RNA.

31. The isolated nucleic acid molecule of claim 28, wherein said nucleic acid molecule is single-stranded.

32. An isolated nucleic acid molecule comprising a polynucleotide sequence complimentary to the polynucleotida sequence of claim 31.

33. The isolated nucleic acid molecule of claim 28, wherein said polynucleotide sequence comprises a heterologous polynucleotide sequence.

34. The isolated nucleic acid molecule of claim 23, wherein said heterologous polynucleotide sequence encodes a heterologous polypeptide.

35. A method for making a recombinant vector comprising inserting the isolated nucleic acid molecule of claim 28 into a vector.

36. A recombinant vector comprising the isolated nucleic acid molecule of claim 28.

37. The recombinant vector of claim 36, wherein said nucleic acid molecule is operably associated with a heterologous regulatory sequence that controls gene expression.

38. A recombinant host cell comprising the isolated nucleic acid molecule of claim 28.

39. The recombinant host cell of claim 38, wherein said nucleic acid molecule is operably associated with a heterologous regulatory sequence that controls gene expression.

40. A method for producing a polypeptide, comprising:
   (a) culturing a host cell under conditions suitable to produce a polypeptide encoded by the polynucleotide of claim 28; and
   (b) recovering the polypeptide from the cell culture.

41. An isolated nucleic acid molecule comprising: a polynucleotide sequence encoding at least 30 contiguous amino acid residues of a human inositol monophosphatase polypeptide encoded by the human cDNA clone contained in ATCC Deposit No. 75753.

42. The isolated nucleic acid molecule of claim 41, wherein said polynucleotide sequence encodes at least 50 amino acid residues of the human inositol monophosphatase polypeptide encoded by the human cDNA clone contained in ATCC Deposite No. 75753.

43. The isolated nucleic acid molecule of claim 41, wherein said nucleic acid molecule is DNA.

44. The isolated nucleic acid molecule of claim 41, wherein said nucleic acid molecule is RNA.

45. The isolated nucleic acid molecule of claim 41, wherein said nucleic acid molecule is single-stranded.

46. An isolated nucleic acid molecule comprising a polynucleotide sequence complimentary to the polynucleotide sequence of claim 45.

47. The isolated nucleic acid molecule of claim 41, wherein said polynucleotide sequence comprises a heterologous polynucleotide sequence.

48. The isolated nucleic acid molecule of claim 47, wherein said heterologous polynucleotide sequence encodes a heterologous polypeptide.

49. A method for making a recombinant vector comprising inserting the isolated nucleic acid molecule of claim 41 into a vector.

50. A recombinant vector comprising the isolated nucleic acid molecule of claim 41.

51. The recombinant vector of claim 50, wherein said nucleic acid molecule is operably associated with a heterologous regulatory sequence that controls gene expression.

52. A recombinant host cell comprising the isolated nucleic acid molecule of claim 41.

53. The recombinant host cell of claim 52, wherein said nucleic acid molecule is operably associated with a heterologous regulatory sequence that controls gene expression.

54. A method for producing a polypeptide, comprising:
   (a) culturing a host cell under conditions suitable to produce a polypeptide encoded by the polynucleotide of claim 41; and
   (b) recovering the polypeptide from the cell culture.

55. A method of using the polynucleotide of claim 1 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

56. A method of using the polynucleotide of claim 5 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

57. A method of using the polynucleotide of claim 14 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

58. A method of using the polynucleotide of claim 19 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

59. A method of using the polynucleotide of claim 28 to detect a nucleic acid molecule in a biological sample which hybridizes thereto comprising:
   (a) obtaining a biological sample suspected of containing said nucleic acid molecule,
   (b) contacting said biological sample with said polynucleotide under conditions suitable for hybridization of said polynucleotide to said nucleic acid molecule; and
   (c) determining the presence or absence of said nucleic acid molecule in said biological sample.

60. A method of using the polynucleotide of claim 33 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

61. A method of using the polynucleotide of claim 41 to detect a nucleic acid molecule in a biological sample which hybridizes thereto comprising:
   (a) obtaining a biological sample suspected of containing said nucleic acid molecule;
   (b) contacting said biological sample with said polynucleotide under conditions suitable for hybridization of said polynucleotide to said nucleic acid molecule; and
   (c) determining the presence or absence of said nucleic acid molecule in said biological sample.

* * * * *